United States Patent
Schulz et al.

(10) Patent No.: US 7,858,376 B2
(45) Date of Patent: Dec. 28, 2010

(54) NINHYDRIN AND IONIC LIQUID REAGENT MIXTURE AND METHOD FOR THE VISUALIZATION OF AMINO ACIDS AND PEPTIDES

(75) Inventors: Michael Schulz, Darmstadt (DE); Heinz-Emil Hauck, Gross-Umstadt (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 12/375,740

(22) PCT Filed: Jul. 3, 2007

(86) PCT No.: PCT/EP2007/005868
§ 371 (c)(1),
(2), (4) Date: Jan. 30, 2009

(87) PCT Pub. No.: WO2008/014859
PCT Pub. Date: Feb. 7, 2008

(65) Prior Publication Data
US 2009/0258427 A1     Oct. 15, 2009

(30) Foreign Application Priority Data
Jul. 31, 2006  (DE) .................. 10 2006 035 515

(51) Int. Cl.
*G01N 33/00* (2006.01)
*C07C 49/00* (2006.01)
(52) U.S. Cl. ......................................... 436/86; 568/327
(58) Field of Classification Search .................. 436/86; 568/309, 327
See application file for complete search history.

(56) References Cited

U.S. PATENT DOCUMENTS 4,299,771 A * 11/1981 Takeshita et al. ............ 552/239

OTHER PUBLICATIONS

Cerbulis ("Pyridine as a Reagent for Detection of Acids on Paper Chromatograms," Analytical Chemistry 1963, 35, 114).*

Yen ("Synthesis of tetrahydro-b-carbolinediketopiperazines in [bdmim][PF6] ionic liquid accelerated by controlled microwave heating," Tetrahedron Lett. 2004, 45, 8137-8140).*

Rochester ("Thin Layer Chromatography (TLC) Notes," 2 pages, [online], [retrieved on Jan. 27, 2010]. Retrieved from the Internet: <URL: http://web.archive.org/web/20060502011211/http://www.chem.rochester.edu/~nvd/tlcnotes.html> Publicly available on May 2, 2006).*

Aldrich Handbook of Fine Chemicals and Laboratory Equipment, 2003-2004 edition., Wilwaukee, Wisconsin., pp. 1000, 1337, and T141.*

Baczek et al. "Behavior of Peptides and Computer-Assisted Optimization of Peptides Separations in a Normal-Phase Thin-Layer Chromatography System with and Without the Addition of Ionic Liquid in the Eluent." XP002454070 BiomedicalChromatography 19.1 (2005): 1-8.

Baczek et al. "Ionic Liquids as Novel Solvent Additives to Separate Peptides." XP009090441 C, Journal of Biosciences 61. 11-12 (2006): 827-832.

Berthod et al. "Nonmolecular Solvents in Separation Methods: Dual Nature of Room Temperature Ionic Liquids." Analytical Chemistry 77.13 (2005): 4071-4080.

Hansen et al. "The Development of Novel Ninhydrin Analogues." XP009090521 Chemical Society Reviews 34.5 (2005): 408-417.

Zabet-Moghaddam et al. "Matrix-Assisted Laser Desorption/Ionization Mass Spectrometry for the Characterization of Ionic Liquids and the Analysis of Amino Acids, Peptides and Proteins in Ionic Liquids." XP002454071 Journal of Mass Spectrometry 39.12 (2004): 1494-1505.

Khawas et al. "A New Reagent for Identification of Amino Acids on Thin-Layer Chromatography Plates." Journal of Planar Chromatography Jul./Aug. 17, 2004: 314-315.

* cited by examiner

*Primary Examiner* — Yelena G Gakh
*Assistant Examiner* — Michelle M Adams
(74) *Attorney, Agent, or Firm* — Millen, White, Zelano & Branigan, P.C.

(57) ABSTRACT

The invention relates to a method and reagent mixture for the staining and thus visualization of amino acids, peptides and similar compounds, in particular after separation by means of thin-layer chromatography. The staining is carried out using ninhydrin for the detection of amino acids, peptides or proteins in combination with at least one ionic liquid.

17 Claims, No Drawings

NINHYDRIN AND IONIC LIQUID REAGENT MIXTURE AND METHOD FOR THE VISUALIZATION OF AMINO ACIDS AND PEPTIDES

The invention relates to a method and reagent mixture for the staining and thus visualisation of amino acids, peptides and similar compounds, in particular after separation by means of thin-layer chromatography. The staining is carried out using at least one reagent for the detection of amino acids, peptides in combination with at least one ionic liquid.

The analysis of proteins plays an important role in the investigation of cell structures or cell metabolism or cell functions. The analysis of proteins or peptides here encompasses, for example, structural analysis, determination of the molecular weight, determination of a distribution pattern (peptide mapping) or also identification of certain peptides or proteins.

In general, the analysis of proteins or peptides must be preceded by a separation. Known methods for this purpose are, for example, liquid chromatography, ion-exchange chromatography, capillary electrophoresis or gel electrophoresis. The analysis is subsequently carried out, for example, by means of staining or by means of mass spectrometry.

Thin-layer chromatography is also suitable for the separation of proteins, peptides or amino acids. A major advantage of thin-layer chromatography consists in that it is inexpensive and simple to carry out. Furthermore, the separation can be carried out one- or multidimensionally, meaning that the resolution of the separation can be matched to the separation problem.

For compounds containing amino groups, such as proteins, peptides or amino acids, various staining methods are available for the evaluation of a thin-layer chromatographic separation (TLC separation). The best known are staining with ninhydrin (2,2-dihydroxyindane-1,3-dione), with fluorescamine or isatine-5-sulfonic acid. Compared with ninhydrin, fluorescamine offers higher sensitivity. However, neither ninhydrin nor fluorescamine offers additional information on the stained compound since all compounds are stained in the same color. Isatine-5-sulfonic acid stains amino acids selectively, but is not suitable for compounds which consist of a plurality of amino acids since the sensitivity drops very greatly with increasing number of amino acids in the molecule to be investigated.

The object of the present invention is therefore to provide a method or reagent for the selective visualization, in particular for the staining, of amino acids, peptides and proteins which can also be employed, in particular, after TLC separation.

It has been found that a reagent for the detection of amino acids, peptides or proteins, in particular ninhydrin or one of its derivatives, very particularly preferably ninhydrin, in combination with at least one ionic liquid selectively stains amino acids and compounds which consist of a plurality of amino acids. Colorations in a broad color spectrum between yellow, green, blue as far as red to pink are obtained. The sensitivity of the staining here corresponds at least to that of a conventional staining of amino acids with, for example, ninhydrin.

The present invention therefore relates to a reagent mixture at least comprising at least one reagent for the detection of amino acids, peptides or proteins, in particular ninhydrin or one of its derivatives, and an ionic liquid.

In the simplest embodiment of the present invention, the reagent mixture consists only of the reagent for the detection of amino acids, peptides or proteins, in particular ninhydrin or one of its derivatives, and an ionic liquid. The ninhydrin therein is, for example, dissolved in the ionic liquid, so that the ionic liquid additionally functions as solvent.

In a preferred embodiment, the reagent mixture at least comprises
a) a reagent at least comprising at least one reagent for the detection of amino acids, peptides or proteins in at least one solvent and
b) a reagent at least comprising at least one ionic liquid.

In a preferred embodiment, the reagent mixture at least comprises
a) a reagent at least comprising 0.01-10% by weight, preferably 0.1-1% by weight, of ninhydrin in at least one solvent
b) a reagent at least comprising at least one ionic liquid, preferably in at least one solvent.

Ionic liquids or liquid salts are ionic species which consist of an organic cation ($K^+$) and a generally inorganic anion ($A^-$). They do not contain any neutral molecules and usually have melting points below 373 K.

The area of ionic liquids is currently being researched intensively since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The ionic liquids of the general formula $K^+A^-$ are essential for the method according to the invention for visualisation. The anion $A^-$ is preferably selected from the group comprising halides, in particular chloride and bromide, tetrafluoroborate, sulfonates, in particular trifluoromethylsulfonate.

There are no restrictions per se with respect to the choice of the cation $K^+$ of the ionic liquid. However, preference is given to organic cations, particularly preferably ammonium, phosphonium, thiouronium, guanidinium or heterocyclic cations.

Ammonium cations can be described, for example, by the formula (1)

$$[NR_4]^+ \qquad (1),$$

where
R in each case, independently of one another, denotes
H, where all substituents R cannot simultaneously be H,
straight-chain or branched alkyl having 1-20 C atoms,
straight-chain or branched alkenyl having 2-20 C atoms and one or more non-conjugated double bonds,
straight-chain or branched alkynyl having 2-20 C atoms and one or more non-conjugated triple bonds,
saturated, partially or fully unsaturated cycloalkyl having 3-7 C atoms,
which may be substituted by alkyl groups having 1-6 C atoms, where one or more R may be partially or fully substituted by halogens, in particular —F and/or —Cl, or partially by —OR', —CN, —C(O)OH, —C(O)NR'$_2$, —SO$_2$NR'$_2$, —SO$_2$OH, —SO$_2$X, —NO$_2$, and where one or two non-adjacent carbon atoms in R which are not in the α-position may be replaced by atoms and/or atom groups selected from the group —O—, —S—, —S(O)—, —SO$_2$—, —N$^+$R'$_2$—, —C(O)NR'—, —SO$_2$NR'—, —P(O)R'—, where R' may be H, non-, partially or perfluorinated C$_1$- to C$_6$-alkyl, C$_3$- to C$_7$-cycloalkyl, unsubstituted or substituted phenyl, and X may be halogen.

Phosphonium cations can be described, for example, by the formula (2)

$$[PR^2{}_4]^+ \quad (2),$$

where
$R^2$ in each case, independently of one another, denotes
H, $NR'_2$,
straight-chain or branched alkyl having 1-20 C atoms,
straight-chain or branched alkenyl having 2-20 C atoms and one or more non-conjugated double bonds,
straight-chain or branched alkynyl having 2-20 C atoms and one or more non-conjugated triple bonds,
saturated, partially or fully unsaturated cycloalkyl having 3-7 C atoms,
which may be substituted by alkyl groups having 1-6 C atoms, where one or more $R^2$ may be partially or fully substituted by halogens, in particular —F and/or —Cl, or partially by —OR', —CN, —C(O)OH, —C(O)NR'$_2$, —SO$_2$NR'$_2$, —SO$_2$OH, —SO$_2$X, —NO$_2$, and where one or two non-adjacent carbon atoms in $R^2$ which are not in the α-position may be replaced by atoms and/or atom groups selected from the group —O—, —S—, —S(O)—, —SO$_2$—, —N$^+$R'$_2$—, —C(O)NR'—, —SO$_2$NR'—, —P(O)R'—, where R'=H, non-, partially or perfluorinated $C_1$- to $C_6$-alkyl, $C_3$— to $C_7$-cycloalkyl, unsubstituted or substituted phenyl, and X=halogen.

However, cations of the formulae (1) and (2) in which all four or three substituents R and $R^2$ are fully substituted by halogens are excluded, for example the tris(trifluoromethyl) methylammonium cation, the tetra(trifluoromethyl)ammonium cation or the tetra(nonafluorobutyl)ammonium cation.

Suitable thiouronium cations can be described by the formula (3)

$$[(R^3R^4N)-C(=SR^5)(NR^6R^7)]^+ \quad (3),$$

where
$R^3$ to $R^7$ each, independently of one another, denote
hydrogen,
straight-chain or branched alkyl having 1 to 20 C atoms,
straight-chain or branched alkenyl having 2-20 C atoms and one or more non-conjugated double bonds,
straight-chain or branched alkynyl having 2-20 C atoms and one or more non-conjugated triple bonds,
saturated, partially or fully unsaturated cycloalkyl having 3-7 C atoms,
which may be substituted by alkyl groups having 1-6 C atoms, where one or more of the substituents $R^3$ to $R^7$ may be partially or fully substituted by halogens, in particular —F and/or —Cl, or partially by —OH, —OR', —CN, —C(O)OH, —C(O)NR'$_2$, —SO$_2$NR'$_2$, —SO$_2$OH, —SO$_2$X, —NO$_2$, and where one or two non-adjacent carbon atoms in $R^3$ to $R^7$ which are not in the α-position may be replaced by atoms and/or atom groups selected from the group —O—, —S—, —S(O)—, —SO$_2$—, —N$^+$R'$_2$—, —C(O)NR'—, —SO$_2$NR'—, —P(O)R'—, where R'=H, non-, partially or perfluorinated $C_1$- to $C_6$-alkyl, $C_3$- to $C_7$-cycloalkyl, unsubstituted or substituted phenyl, and X=halogen.

Guanidinium cations can be described by the formula (4)

$$[C(NR^8R^9)(NR^{10}R^{11})(NR^{12}R^{13})]^+ \quad (4),$$

where
$R^8$ to $R^{13}$ each, independently of one another, denote
hydrogen, —CN, $NR'_2$,
straight-chain or branched alkyl having 1 to 20 C atoms,
straight-chain or branched alkenyl having 2-20 C atoms and one or more non-conjugated double bonds,
straight-chain or branched alkynyl having 2-20 C atoms and one or more non-conjugated triple bonds,
saturated, partially or fully unsaturated cycloalkyl having 3-7 C atoms,
which may be substituted by alkyl groups having 1-6 C atoms, where one or more of the substituents $R^8$ to $R^{13}$ may be partially or fully substituted by halogens, in particular —F and/or —Cl, or partially by —OR', —CN, —C(O)OH, —C(O)NR'$_2$, —SO$_2$NR'$_2$, —SO$_2$OH, —SO$_2$X, —NO$_2$, and where one or two non-adjacent carbon atoms in $R^8$ to $R^{13}$ which are not in the α-position may be replaced by atoms and/or atom groups selected from the group —O—, —S—, —S(O)—, —SO$_2$—, —N$^+$R'$_2$—, —C(O)NR'—, —SO$_2$NR'—, —P(O)R'—, where R'=H, non-, partially or perfluorinated $C_1$- to $C_6$-alkyl, $C_3$- to $C_7$-cycloalkyl, unsubstituted or substituted phenyl, and X=halogen.

In addition, it is possible to employ cations of the general formula (5)

$$[HetN]^+ \quad (5),$$

where
HetN$^+$ denotes a heterocyclic cation selected from the group

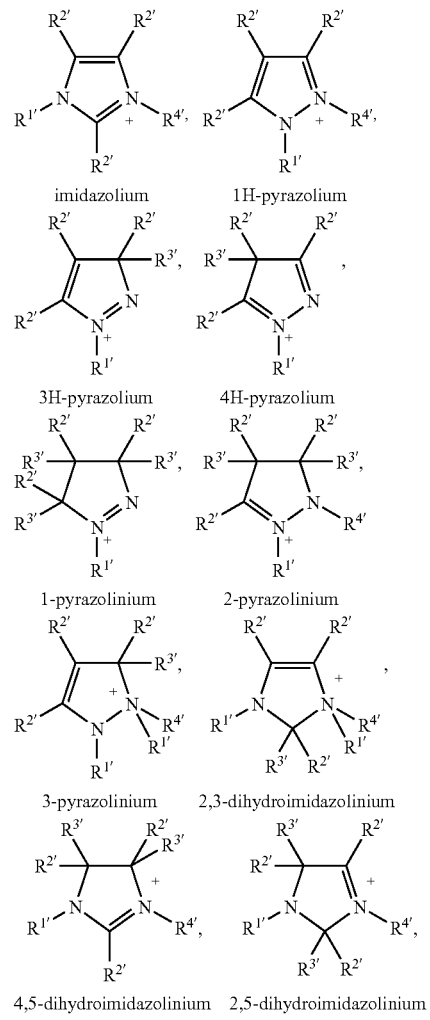

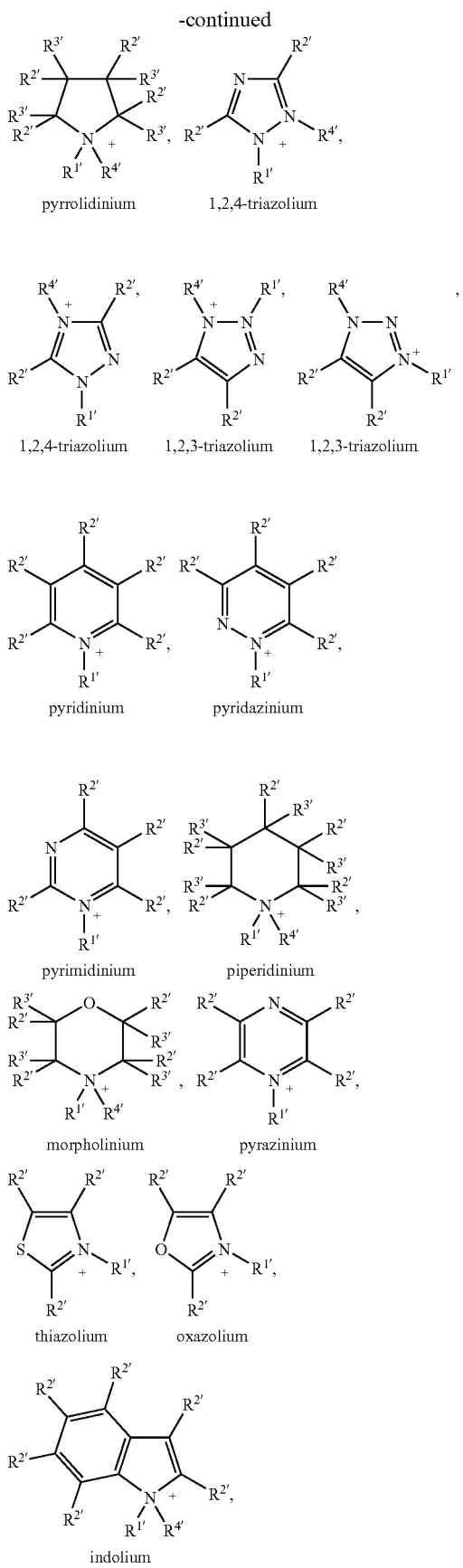

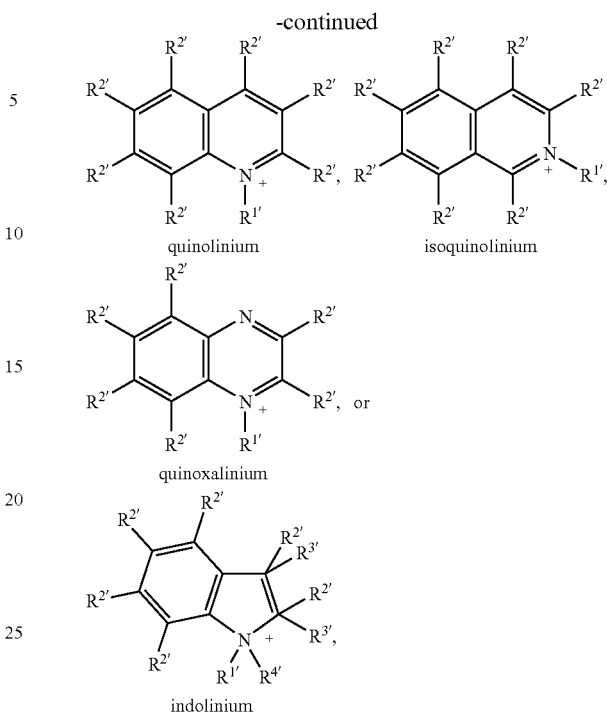

where the substituents
R$^{1'}$ to R$^{4'}$ each, independently of one another, denote hydrogen, —CN,
straight-chain or branched alkyl having 1-20 C atoms,
straight-chain or branched alkenyl having 2-20 C atoms and one or more non-conjugated double bonds,
straight-chain or branched alkynyl having 2-20 C atoms and one or more non-conjugated triple bonds,
saturated, partially or fully unsaturated cycloalkyl having 3-7 C atoms,
which may be substituted by alkyl groups having 1-6 C atoms,
saturated, partially or fully unsaturated heteroaryl, heteroaryl-C$_1$-C$_6$-alkyl or aryl-C$_1$-C$_6$-alkyl,
where the substituents R$^{1'}$, R$^{2'}$, R$^{3'}$ and/or R$^{4'}$ together may also form a ring system,
where one or more substituents R$^{1'}$ to R$^{4'}$ may be partially or fully substituted by halogens, in particular —F and/or —Cl, or —OR', —CN, —C(O)OH, —C(O)NR'$_2$, —SO$_2$NR'$_2$, —C(O)X, —SO$_2$OH, —SO$_2$X, —NO$_2$, but where R$^{1'}$ and R$^{4'}$ cannot simultaneously be fully substituted by halogens, and where, in the substituents R$^{1'}$ to R$^{4'}$, one or two non-adjacent carbon atoms which are not bonded to the heteroatom may be replaced by atoms and/or atom groups selected from the group —O—, —S—, —S(O)—, —SO$_2$—, —N$^+$R'$_2$—, —C(O)NR'—, —SO$_2$NR'—, —P(O)R'—, where R'=H, non-, partially or perfluorinated C$_1$- to C$_6$-alkyl, C$_3$- to C$_7$-cycloalkyl, unsubstituted or substituted phenyl, and X=halogen.

Suitable as substituent R$^{2'}$ are, in particular, also atom groups selected from —OR', —NR'$_2$, —C(O)OH, —C(O)NR'$_2$, —SO$_2$NR'$_2$, —SO$_2$OH, —SO$_2$X or —NO$_2$.

For the purposes of the present invention, fully unsaturated substituents are also taken to mean aromatic substituents.

In accordance with the invention, suitable substituents R and R$^2$ to R$^{13}$ of the compounds of the formulae (1) to (4), besides hydrogen, are preferably: C$_1$- to C$_{20}$-, in particular C$_1$- to C$_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R and $R^2$ in the compounds of the formula (1) or (2) may be identical or different. The substituents R and $R^2$ are preferably different.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

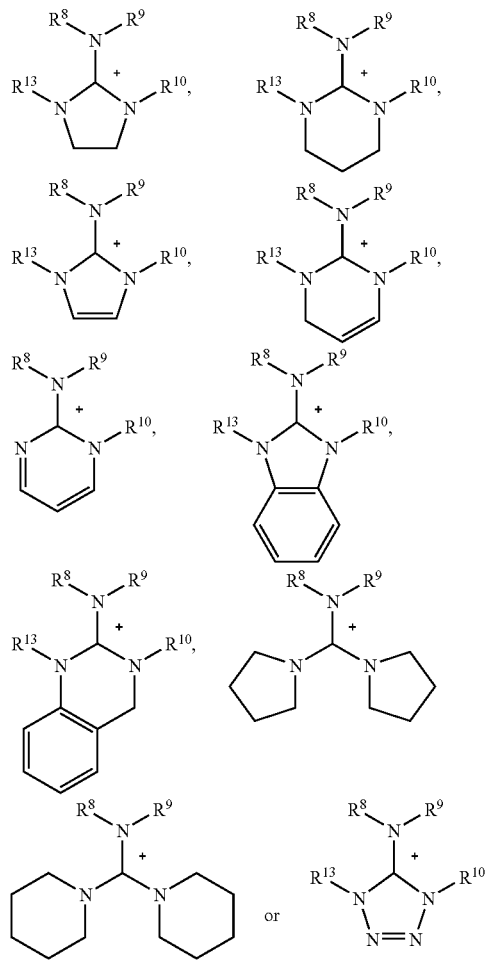

where the substituents $R^8$ to $R^{10}$ and $R^{13}$ can have a meaning or particularly preferred meaning indicated above.

If desired, the carbocyclic or heterocyclic rings of the guanidinium cations indicated above may also be substituted by $C_1$- to $C_6$-alkyl, $C_1$- to $C_6$-alkenyl, $NO_2$, CN, $NR'_2$, F, Cl, Br, I, $C_1$-$C_6$-alkoxy, $SCF_3$, $SO_2CF_3$, COOH, $SO_2NR'_2$, $SO_2X'$ or $SO_3H$, where X and R' have a meaning indicated above, substituted or unsubstituted phenyl or an unsubstituted or substituted heterocycle.

Up to four substituents of the thiouronium cation $[(R^3R^4N)C(=SR^5)(NR^6R^7)]^+$ may also be bonded in pairs in such a way that mono-, bi- or polycyclic cations are formed.

Without restricting generality, examples of such cations are indicated below, where Y=S:

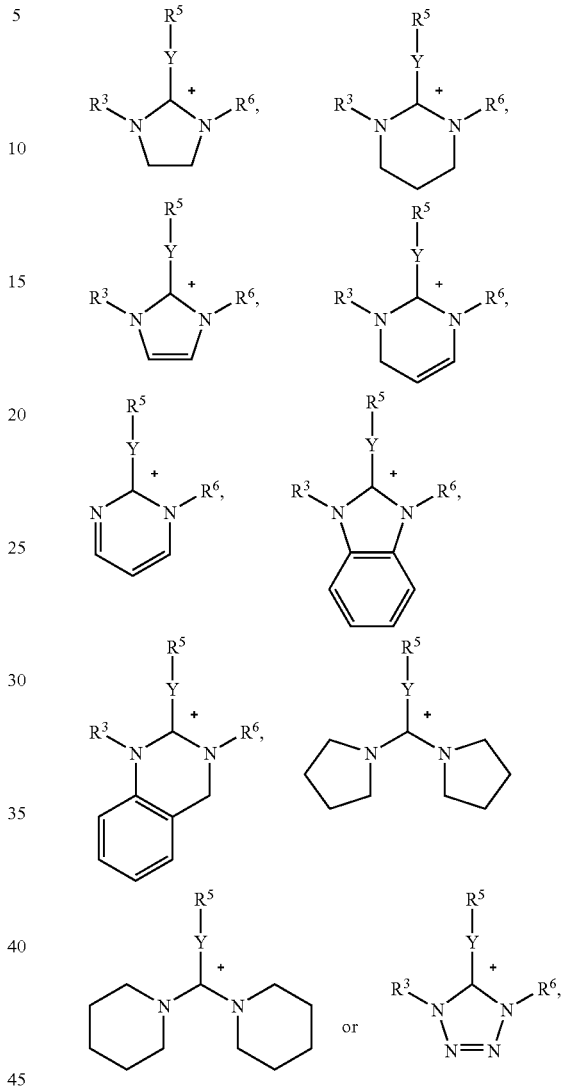

where the substituents $R^3$, $R^5$ and $R^6$ can have a meaning or particularly preferred meaning indicated above.

If desired, the carbocyclic or heterocyclic rings of the cations indicated above may also be substituted by $C_1$- to $C_6$-alkyl, $C_1$- to $C_6$-alkenyl, $NO_2$, CN, $NR'_2$, F, Cl, Br, I, $C_1$-$C_6$-alkoxy, $SCF_3$, $SO_2CF_3$, COOH, $SO_2NR'_2$, $SO_2X$ or $SO_3H$ or substituted or unsubstituted phenyl or an unsubstituted or substituted heterocycle, where X and R' have a meaning indicated above.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (3) to (4) may be identical or different. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (5), besides hydrogen, are preferably: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular hydrogen, methyl, ethyl, isopropyl, propyl, butyl, sec-butyl, tertbutyl, cyclohexyl, phenyl or benzyl. $R^{2'}$ is particularly preferably hydrogen, methyl, ethyl, isopropyl, propyl, butyl or sec-butyl. $R^{2'}$ and $R^{3'}$ are very particularly preferably hydrogen.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl, optionally difluoromethyl, trifluoromethyl, pentafluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OR', —NR'$_2$, —CN, —C(O)OH, —C(O)NR'$_2$, —SO$_2$NR'$_2$, —C(O)X, —SO$_2$OH, —SO$_2$X, —NO$_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclohexenyl, phenyl, cycloheptenyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OR', —CN, —C(O)OH, —C(O)NR'$_2$, —SO$_2$NR'$_2$, —SO$_2$OH, —SO$_2$X, —NO$_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —N$^+$R'$_2$—, —C(O)NR'—, —SO$_2$NR'—, —P(O)R'—, where R'=non-, partially or perfluorinated $C_2$- to $C_6$-alkyl, $C_3$- to $C_7$-cycloalkyl, unsubstituted or substituted phenyl.

Without restricting generality, examples of substituents R, $R^2$ to $R^{13}$ and $R^{1'}$ to $R^{4'}$ modified in this way are:
—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$SC$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$ or P(O)(C$_2$H$_5$)$_2$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, NO$_2$, CN, NR'$_2$, F, Cl, Br, I, $C_1$-$C_6$-alkoxy, SCF$_3$, SO$_2$CF$_3$, COOH, SO$_2$X', SO$_2$NR''$_2$ or SO$_3$H, where X' denotes F, Cl or Br and R'' denotes a non-, partially or perfluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, NO$_2$, CN, NR'$_2$, F, Cl, Br, I, $C_1$-$C_6$-alkoxy, SCF$_3$, SO$_2$CF$_3$, COOH, SO$_2$X', SO$_2$NR'$_2$ or SO$_3$H, where X' and R' have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl, pyridinylhexyl, where the heterocyclic radicals described above may furthermore be linked to the alkylene chain in this way.

HetN+ is preferably

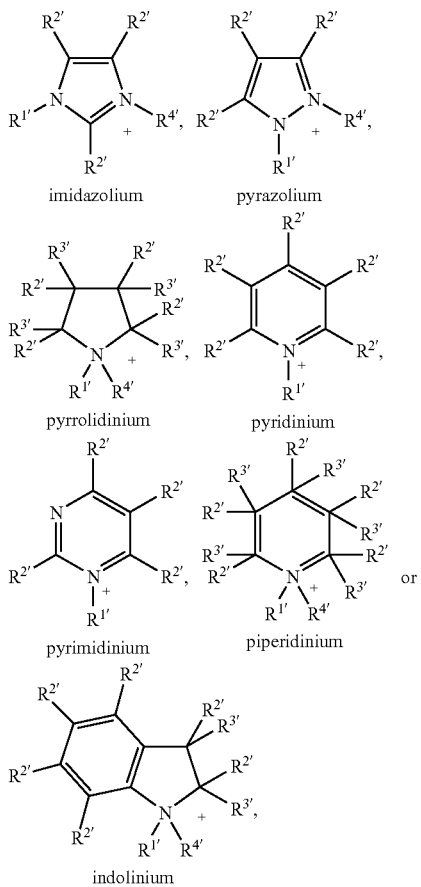

where the substituents R$^{1'}$ to R$^{4'}$ each, independently of one another, have a meaning described above.

The cations of the ionic liquid according to the invention are preferably ammonium, imidazolium, pyridinium, pyrrolidinium, piperidinium, phosphonium, morpholinium or piperidinium cations.

Particularly preferred ionic liquids are 1-pentyl-3-methylimidazolium chloride, 1-hexyl-3-methylimidazolium chloride, 1-heptyl-3-methylimidazolium chloride, 1-octyl-3-methylimidazolium chloride, 1-nonyl-3-methylimidazolium chloride, 1-decyl-3-methylimidazolium chloride, trihexyltetradecylphosphonium chloride, ethyldimethylpentylammonium bromide, ethyldimethylpropylammonium chloride, 1-methyl-1-octylpyrrolidinium chloride, n-butylpyridinium chloride, n-octylpyridinium chloride, 4-methyl-4-pentylmorpholinium bromide or 1-methyl-1-pentylpiperidinium bromide.

Very particularly preferred ionic liquids are 1-pentyl-3-methylimidazolium chloride, 1-hexyl-3-methylimidazolium chloride, 1-heptyl-3-methylimidazolium chloride, 1-octyl-3-methylimidazolium chloride, 1-nonyl-3-methylimidazolium chloride, 1-decyl-3-methylimidazolium chloride, ethyldimethylpentylammonium bromide and 1-methyl-1-octylpyrrolidinium chloride.

In another preferred embodiment, the reagent mixture additionally comprises at least one TLC plate.

The present invention furthermore relates to a method for the analysis of a sample comprising amino acids, peptides and/or proteins by
a) chromatographic separation of the sample on a thin-layer chromatography plate (TLC plate)
b) staining of the separated sample on the TLC plate with a reagent mixture at least comprising at least one reagent for the detection of amino acids, peptides or proteins and at least one ionic liquid.

The present invention furthermore relates to a method for the analysis of a sample comprising amino acids, peptides and/or proteins by
a') chromatographic separation of the sample on a thin-layer chromatography plate (TLC plate), where the mobile phase comprises at least one ionic liquid, and
b') staining of the separated sample on the TLC plate with a reagent mixture at least comprising at least one reagent for the detection of amino acids, peptides or proteins.

The present invention likewise relates to a method for the analysis of a sample comprising amino acids, peptides and/or proteins by chromatographic separation of the sample on a thin-layer chromatography plate (TLC plate), where the mobile phase comprises at least one reagent for the detection of amino acids, peptides or proteins, preferably ninhydrin or one of its derivatives, and at least one ionic liquid.

In a preferred embodiment, the TLC plate employed in step a) or a') is a plate having a nonpolar phase or a cellulose phase.

In another preferred embodiment, the visualisation in step b) is carried out by treating the TLC plate in a step b1) firstly with a reagent which at least comprises an ionic liquid and subsequently in a step b2) with a reagent which at least comprises at least one reagent for the detection of amino acids, peptides or proteins, preferably ninhydrin or one of its derivatives. It is also possible to carry out the visualisation in step b) by firstly carrying out a treatment with at least one reagent for the detection of amino acids, peptides or proteins, preferably ninhydrin (b2), and then with the ionic liquid (b1). However, the visualisation in step b) is preferably carried out by treating the TLC plate in a step b1) firstly with a reagent which at least comprises an ionic liquid and subsequently in a step b2) with a reagent which at least comprises ninhydrin or one of its derivatives.

In a preferred embodiment, the TLC plate is heated in step b) to a temperature between 50 and 200° C. for 0.5 to 10 minutes after treatment with the reagent mixture at least comprising at least one reagent for the detection of amino acids, peptides or proteins, preferably ninhydrin, and at least one ionic liquid or after step b').

In a preferred embodiment, use is made of a reagent mixture which comprises a reagent which at least comprises 0.01-10% by weight, preferably 0.1-1% by weight, of ninhydrin in at least one solvent, and a reagent which at least comprises 0.1 to 10% of at least one ionic liquid in at least one solvent.

The present invention additionally relates to a method for the visualisation, in particular for the staining, of amino acids, peptides and/or proteins, characterized in that the amino acids, peptides and/or proteins are treated with a reagent combination which at least comprises an ionic liquid and at least one reagent for the detection of amino acids, peptides or proteins, preferably ninhydrin or one of its derivatives.

In a preferred embodiment, the amino acids, peptides and/or proteins are firstly treated with a reagent which at least comprises an ionic liquid and then with a reagent which at least comprises ninhydrin.

Further combinations or preferred embodiments are disclosed in the patent claims.

A sample comprising amino acids, peptides and/or proteins is, in accordance with the invention, a sample which is assumed to comprise at least one amino acid and/or peptide. The sample can be of natural or synthetic origin, for example a cell extract, a body fluid, a protein digestion or reaction mixture from a peptide synthesis. In general, it is a liquid sample, where the analytes are typically present in an organic solvent or water or mixtures of organic solvents or mixtures of organic solvents and water. The sample can comprise any desired further solid, emulsified or dissolved constituents, which, however, should interfere neither with the TLC separation nor with the later staining of the analytes (amino acids and/or peptides).

Solid samples are generally firstly taken up in one of the above-mentioned solvents in order that they can be applied to the TLC plate. In the case of concentrated samples, it may be necessary firstly to dilute them. It is known to the person skilled in the art in the area of thin-layer chromatography how large the amount of sample and sample concentration may or must be, depending on the TLC plate employed and the particular separation problem, in order to obtain bands which can be evaluated as ideally as possible.

In accordance with the invention, amino acids, peptides and/or proteins are all natural or synthetic amino acids, compounds which contain two or more natural or synthetic amino acids and amino-containing compounds which can be stained, for example, with a conventional ninhydrin staining. Compounds which contain two or more natural or synthetic amino acids are preferably oligoamino acids or peptides, in particular peptides having a chain length of up to 150 amino acids, preferably having a chain length of between 2 and 100, particularly preferably between 2 and 25, amino acids. Examples of amino-containing compounds which can be stained with a conventional ninhydrin staining are amino acids, amines or amino sugars. The amino acids can be synthetic or natural amino acids. They are preferably natural amino acids, such as Ala, Arg, Asn, Asp, Cys, Gln, Glu, Gly, His, Ile, Leu, Lys, Met, Phe, Pro, Ser, Thr, Typ, Tyr or Val.

If it is desired to analyse proteins or peptides having a chain length of greater than 150 amino acids using the method according to the invention, these can, in a further embodiment, firstly be cleaved to give peptides having a chain length of less than 150 amino acids—for example by tryptic digestion.

In accordance with the invention, a TLC plate is any medium on which a thin-layer chromatographic separation can be carried out. In general, a TLC plate consists of a support, for example in the form of a glass plate, metal plate or foil or a plastic film which is covered or coated with a sorbent phase. The sorbents used are typically the base sorbents known for chromatographic purposes. These are, for example, silica gel, aluminum oxide, cellulose, kieselguhr or other organic or inorganic polymers or organic/linorganic hybrid polymers. The base sorbents may furthermore be derivatized with functional groups which modify their separation properties. Examples thereof are RP phases, in which, for example, silica gel has been derivatized with ligands which have C8 or C18 chains (reversed phase material). Other examples are CN or diol-modified phases. An overview of common sorbent phases for TLC is given in Klaus K. Unger, *Packings and Stationary Phases in Chromatographic Techniques*, M. Decker, New York 1990. The sorbent phases can be divided into polar, moderately polar and nonpolar phases in accordance with the polarity of their surface. It has been found that the reagent mixture according to the invention is particularly suitable for staining amino acids and/or peptides on nonpolar phases, such as kieselguhr or reversed phase materials. Cellulose phases can also be stained with excellent color quality and intensity.

A reagent mixture according to the invention at least comprises at least one reagent for the detection of amino acids, peptides or proteins, preferably ninhydrin, and at least one ionic liquid. The reagent mixture can be in the form of a reagent, typically a liquid reagent, or comprise a plurality of different reagents or components. The at least one reagent for the detection of amino acids, peptides or proteins, preferably ninhydrin, and at least one ionic liquid may be present together in one reagent or in two different reagents or components of the reagent mixture.

In an embodiment, the reagent mixture consists at least of a typically liquid reagent which at least comprises at least one reagent for the detection of amino acids, peptides or proteins, preferably ninhydrin, and at least one ionic liquid.

In a preferred embodiment, the reagent mixture at least consists of
a) a reagent which at least comprises ninhydrin or one of its derivatives,
b) a reagent which at least comprises an ionic liquid.

Both reagents are typically liquid.

Solvents which can be employed are one or more organic solvents or mixtures of one or more organic solvents with water or water. It is also possible for the ionic liquid itself to serve as solvent and, for example in accordance with the embodiment described above, to function as solvent for the reagent for the detection of amino acids, peptides and/or proteins. A plurality of solvents may be present, but preferably only one solvent is used. For ionic liquids which have low solubility in organic solvents, water or a mixture of water+alcohol may be appropriate.

In the case of a reagent which comprises, for example, ninhydrin and at least one ionic liquid, acetone or propanol preferably serves as solvent. In the case of a reagent which comprises ninhydrin, but no ionic liquid, an organic solvent, such as propanol or acetone, preferably serves as solvent. In the case of a reagent which comprises at least one ionic liquid, but no ninhydrin, acetone, propanol, water and water/alcohol mixtures preferably serve as solvent.

In addition, the reagents may optionally comprise further substances, for example one or more additional ionic liquids, solvents, stabilisers, buffers, further dyes, etc.

Ninhydrin is typically present in the reagents according to the invention in concentrations between 0.01 and 10% by weight, preferably in concentrations between 0.1 and 1% by weight.

The ionic liquid can, depending on the nature of the reagent mixture, be present in concentrations between 0.1 and 100% by weight. If the ionic liquid at the same time serves as solvent, or if the reagent mixture comprises separate reagents of, for example, ninhydrin and ionic liquid, the proportion of ionic liquid is typically between 80 and 100%. It goes without saying that, in the case of the embodiment in which, for example, ninhydrin and the ionic liquid are present together, the proportion of ionic liquid cannot be 100%, but instead must be reduced corresponding to the content of ninhydrin.

If, in addition, another solvent is used, the ionic liquid is typically present in concentrations between 0.1 and 15% by weight, preferably in concentrations between 0.1 and 10% by weight, particularly preferably in concentrations between 1 and 5% by weight. If a reagent comprises two or more different ionic liquids, the above concentration data then apply to the total amount of ionic liquid.

Examples of reagent combinations according to the invention are:

1. A reagent combination consisting of a reagent which at least comprises between 0.01 and 10% of ninhydrin and between 0.1 and 10% of one or more ionic liquids in a solvent.
2. A reagent combination comprising
   a) a reagent which at least comprises between 0.01 and 10% of ninhydrin in a solvent
   b) a reagent which at least comprises between 0.1 and 10% of one or more ionic liquids in a solvent.
3. A reagent combination corresponding to variant 2 which additionally comprises a further reagent which at least comprises one or more ionic liquids in a solvent, where the nature, concentration and/or composition of the ionic liquids of this additional reagent differs from those of the other reagent which at least comprises one or more ionic liquids in a solvent.
4. A reagent combination corresponding to variant 1, 2 or 3, additionally comprising one or more TLC plates and/or alternative staining reagents (for example reagents for fluorescamine staining) and/or color tables or color patterns for evaluation of the staining results.

Preferred reagent combinations comprise two or more reagents, where ninhydrin on the one hand and one or more ionic liquids on the other hand are present separately in different reagents.

In the method according to the invention for the analysis of a sample comprising amino acids, peptides and/or proteins, the sample is firstly applied to a TLC plate and separated by thin-layer chromatography. The performance of a thin-layer chromatographic separation is known to the person skilled in the art, for example from Dünnschichtchromatographie, Praktische Durchführung and Fehlervermeidung [Thin-Layer Chromatography, Practical Performance and Error Avoidance] by Elke Hahn-Deinstrop, Wiley-VCH (1998). The separation can be carried out one-dimensionally or multidimensionally.

When the thin-layer chromatographic separation is complete, the staining is carried out with a reagent mixture at least comprising ninhydrin and at least one ionic liquid for visualisation of the amino acids, peptides and/or proteins present in the sample. To this end, the TLC plate is preferably firstly dried slightly, preferably completely, in order that the mobile phase used in the TLC separation is removed in full or part. However, the staining according to the invention can also be carried out on TLC plates still moistened with the mobile phase.

The application of the reagent combination according to the invention, i.e. generally the wetting of the TLC plate with the reagents of the reagent mixture, is typically carried out by dipping the TLC plate into the corresponding liquid reagents or preferably by spraying the reagents onto the TLC plate.

In an embodiment, the TLC plate is wetted with a reagent which at least comprises ninhydrin and one or more ionic liquids in a solvent. This reagent may already have been prepared some time before its use or may preferably have been mixed together a maximum of 24 hours before its use.

In a preferred embodiment, the TLC plate is firstly wetted with a reagent which at least comprises an ionic liquid in at least one solvent. The plate is subsequently, preferably after full or partial drying of the TLC plate, wetted with a reagent which at least comprises ninhydrin.

Depending on the nature of the amino acids, peptides and/or proteins to be stained, the color reaction can occur spontaneously or after an incubation time of a number of hours or, as in the most frequent cases, only after heating. For this reason, the TLC plate is preferably heated to temperatures above 35° C., preferably above 50° C., after application of the reagents of the reagent combination according to the invention. In a particularly preferred embodiment, the plate is heated to temperatures of between 50 and 200° C. The duration of the temperature treatment is generally between 0.5 and 10 minutes.

The coloration forming can be evaluated visually or using corresponding optical instruments.

The reagent combination according to the invention can also be used for staining amino acids, peptides and/or proteins in other media, for example in the liquid phase or on other supports, such as paper, gels or membranes. The reagent combination can equally be employed for a rapid test in which it is firstly only determined generally whether amino acids, peptides and/or proteins are present in a sample. To this end, there is no need to carry out a chromatographic or other separation. It is sufficient to bring the sample—preferably on a support, for example a TLC plate—into contact with the reagent combination. The procedure corresponds to step b) of the method described above. It can then be determined from the color development whether and possibly which amino acids, peptides and/or proteins are present in the sample.

The particular advantage of the reagent mixture according to the invention or the method according to the invention is that a different coloration forms for different amino acids, peptides and/or proteins. Whereas all amino acids and/or peptides apart from proline exhibit a blue to violet coloration in the case of conventional ninhydrin staining in which no ionic liquids are added, the color in the staining according to the invention varies over the entire color spectrum. In addition, the choice of the ionic liquid or mixture of two or more ionic liquids employed enables the color spectrum forming to be modified. Thus, if necessary, it can be discovered with reference to a few experiments with different ionic liquids which ionic liquid or which mixture is particularly advantageous for the analysis problem present and thus stains the target analytes particularly well and in a distinguishable manner from other amino acids and/or peptides present in the sample.

Both amino acids and also peptides exhibit different colorations after treatment with the reagent combination according to the invention, depending on their chemical structure or composition. This both considerably simplifies identification of certain amino acids in a sample, but also identification of peptides, for example for peptide mapping after tryptic digestion.

Tables 1 and 2 attached list by way of example the color patterns arising on staining of some amino acids for reagent combinations according to the invention with different ionic liquids.

TABLE 1

| Amino acid | Conventional staining with ninhydrin | Staining according to the invention with ninhydrin and ionic liquid: | | | |
|---|---|---|---|---|---|
| | | 1-Pentyl-3-methyl-imidazolium Cl | Trihexyl-tetradecyl-phosphonium Cl | Tetrabutyl-phosphonium Cl | Ethyldimethyl-pentyl-ammonium Br |
| Alanine | violet | blue | violet | turquoise | turquoise |
| Arginine | violet | grey | violet | blue | violet |
| Asparagine | violet | orange | violet | brownish | orange |
| Aspartic acid | violet | turquoise | violet | turquoise | turquoise |
| Cysteine | violet | pink | violet | pink | pink |
| Glutamine | violet | grey | violet | blue | grey |
| Glutamic acid | violet | blue | violet | blue | blue |
| Glycine | violet | violet | violet | blue | brown |
| Histidine | violet | grey-brown | violet | brownish | brown |
| Isoleucine | violet | blue | violet | blue | blue |
| Leucine | violet | black-violet | violet | grey | grey-green |
| Lysine | violet | blue | violet | blue | blue |
| Methionine | violet | brownish | violet | grey | brownish |
| Phenylalanine | violet | grey | violet | blue | violet |
| Proline | yellow | yellow | yellow | yellow | orange |
| Serine | violet | grey | violet | greenish | greenish |
| Threonine | violet | blue | violet | blue | blue |
| Tryptophan | violet | brownish | violet | violet | violet |
| Tyrosine | violet | greyish | violet | greyish | brown |
| Valine | violet | blue | violet | blue | blue |

TABLE 2

| Amino acid | Staining according to the invention with ninhydrin and ionic liquid: | | | | | |
|---|---|---|---|---|---|---|
| | Ethyl-dimethyl-propyl-ammonium Cl | 1-Methyl-1-octyl-pyrrolidinium Cl | n-Butyl-pyridinium Cl | n-Octyl-pyridinium Cl | 4-Methyl-4-pentyl-morpholinium Br | 1-Methyl-1-pentyl-piperidinium Br |
| Alanine | blue | turquoise | blue | turquoise | turquoise | turquoise |
| Arginine | grey | grey | grey | grey | violet | violet |
| Asparagine | orange | orange | brown | orange | orange | orange |
| Aspartic acid | turquoise | turquoise | turquoise | turquoise | turquoise | turquoise |
| Cysteine | red | pink | red | pink | pink | pink |
| Glutamine | greyish | blue-grey | greyish | blue-grey | grey | grey |
| Glutamic acid | blue | blue-grey | blue | blue-grey | blue | blue |
| Glycine | violet | brown | violet | violet | brown | brown |
| Histidine | brown | brownish | brown | brown | brown | brown |
| Isoleucine | blue | blue | blue | blue | blue | blue |
| Leucine | grey | brown-grey | grey | brown-grey | grey-green | grey-green |
| Lysine | blue | blue | blue | blue | blue | blue |
| Methionine | grey | grey | grey | grey | brownish | brownish |
| Phenylalanine | blue | blue | blue | blue | violet | violet |
| Proline | yellow | yellow | yellow | yellow | orange | orange |
| Serine | violet | greenish | violet | greenish | greenish | greenish |
| Threonine | violet | blue | violet | blue | blue | blue |
| Tryptophan | grey | — | grey | grey | violet | violet |
| Tyrosine | grey | — | grey | brownish | brown | brown |
| Valine | blue | — | blue | blue | blue | blue |

The visualisation can usually take place even with amounts of 10 to 50 ng of amino acid or peptide.

Besides ninhydrin, corresponding derivatives of ninhydrin or complexes of ninhydrin, for example those in combination with, for example, Cu, Cd, Sn, can of course also be employed.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below is incorporated into this application by way of reference.

The present invention can comprise, essentially consist of or consist of the said necessary or optional constituents or restrictions.

EXAMPLES

1. Selective Staining Of Amino Acids

| Staining with ionic liquid and ninhydrin |
| --- |
| Substances: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, (from left to right) |
| Mobile phase: 2-butanol/pyridine/acetic acid (100%)/water (30/20/6/24) |
| Stationary phase: ProteoChrom ® HPTLC cellulose aluminum foil (manufacturer Merck KGaA, Germany) |
| Staining: spraying with 3.5% ionic liquid solution, drying, spraying with 0.5% ninhydrin solution and heating to 110° C. |
| Ionic liquid: 1-pentyl-3-methylimidazolium chloride (colors see Table 1) |

2. Selective Staining Of Peptides From Tryptic Digestion Of Proteins

| Staining with ionic liquid and ninhydrin |
| --- |
| Substances: tryptic digestion of phosphitin, myoglobin, cytochrome C, β-casein, BSA (from left to right) |
| Mobile phase: 2-butanol/pyridine/acetic acid (100%)/water (30/20/6/24) |
| Stationary phase: ProteoChrom © HPTLC cellulose aluminum foil (manufacturer Merck KGaA, Germany) |
| Staining: spraying with 3.5% ionic liquid solution, drying, spraying with 0.5% ninhydrin solution and heating to 110° C. |
| Ionic liquid: 1-pentyl-3-methylimidazolium chloride |
| Colors: brown, red, red-brown, blue, violet |

Method Description:

Sample application: The samples are applied to the TLC plate using a capillary or using an automatic TLC application device (for example Linomat V, Camag, Muttenz, Switzerland). For a typical sample concentration of 1-2 mg/ml, 1-10 μl are applied.

Development: The development is carried out in a TLC chamber. The plate is dried briefly after application and then placed in a TLC chamber filled with mobile phase (without chamber saturation) and developed. The development distance is 5 cm and the development time for 5 cm is about 1 h.

Drying: The plate is dried under compressed air for at least 30 min in order to remove the mobile phase as completely as possible.

Staining: The staining is carried out by spraying using a TLC spraying device. To this end, a 3.5% ionic liquid solution and a 0.5% ninhydrin solution are prepared. The plate is firstly sprayed with the ionic liquid solution. Interim drying for 5 min is then carried out, The plate is then sprayed with ninhydrin solution and immediately thereafter heated at 110° C. for two minutes. The plate is briefly cooled and documented.

Alternatively, a fully automatic spraying device, for example the ChromaJet DS 20 device from DESAGA SARSTEDT group (Germany), can also be employed.

The invention claimed is:

1. A reagent mixture for the detection of amino acids, peptides or proteins comprising:
   a first reagent comprising ninhydrin; and
   at least one other reagent comprising at least one ionic liquid selected from 1-pentyl-3-methylimidazolium chloride, 1-hexyl-3-methylimidazolium chloride, 1-heptyl-3-methylimidazolium chloride, 1-octyl-3-methylimidazolium chloride, 1-nonyl-3-methylimidazolium chloride, 1-decyl-3-methylimidazolium chloride, trihexyltetradecylphosphonium chloride, ethyldimethylpentylammonium bromide, ethyldimethylpropylammonium chloride, 1-methyl-1-octylpyrrolidinium chloride, n-butylpyridinium chloride, n-octylpyridinium chloride, 4-methyl-4-pentylmorpholinium bromide, and 1-methyl-1-pentylpiperidinium bromide.

2. The reagent mixture according to claim 1, wherein said reagent mixture comprises 0.01-10% by weight of ninhydrin and 0.1-10% by weight said at least one ionic liquid.

3. The reagent mixture according to claim 1, wherein
   a) said first reagent comprises 0.01-10% by weight of ninhydrin in at least one solvent, and
   b) said at least one other reagent comprises 0.1 to 10% by weight of said at least one ionic liquid in at least one solvent.

4. The reagent mixture according to claim 3, wherein said first reagent contains 0.1-1% by weight of ninhydrin.

5. An article comprising said reagent mixture according to claim 3, and at least one TLC plate.

6. An article comprising said reagent mixture according to claim 1, and at least one TLC plate.

7. A method for the visualization of amino acids, peptides and/or proteins, comprising:
   treating amino acids, peptides and/or proteins with a reagent mixture according to claim 1.

8. A method for the analysis of a sample comprising amino acids, peptides and/or proteins, said method comprising:
   a) chromatographic separation of said sample on a thin-layer chromatography plate (TLC plate);
   b) staining of the resultant separated sample on said TLC plate with said reagent mixture according to claim 1.

9. The method according to claim 8, wherein said TLC plate is a plate having a nonpolar phase or a cellulose phase.

10. The method according to claim 8, wherein said TLC plate is heated in step b) to a temperature between 50 and 200° C. for 0.5 to 10 minutes after staining with said reagent mixture according to claim 1.

11. The method according to claim 8, wherein said first reagent comprises 0.01-10% by weight of ninhydrin in at least one solvent, and said at least one other reagent comprises 0.1 to 10% by weight of said at least one ionic liquid in at least one solvent.

12. The method according to claim 11, wherein said first reagent comprises 0.1-1% by weight of ninhydrin.

13. The method according to claim 8, wherein said first reagent and said at least one ionic liquid are together in a liquid reagent.

14. The method according to claim 13, wherein said liquid reagent comprises 0.01-10% by weight of ninhydrin and 0.1-10% by weight of said at least one ionic liquid.

15. A method for the analysis of a sample comprising amino acids, peptides and/or proteins by chromatographic separation, said method comprising subjecting said sample to chromatographic separation on a thin-layer chromatography plate (TLC plate), where the mobile phase used during said chromatographic separation comprises said reagent mixture according to claim 1.

16. The method according to claim 15, wherein said TLC plate is a plate having a nonpolar phase or a cellulose phase.

17. The method according to claim 15, wherein after chromatographic separation said TLC plate is heated to a temperature between 50 and 200° C. for 0.5 to 10 minutes.

* * * * *